(12) United States Patent
Yasui et al.

(10) Patent No.: US 8,859,985 B2
(45) Date of Patent: Oct. 14, 2014

(54) RADIATION DETECTOR, RADIATION DETECTION APPARATUS, AND X-RAY ANALYZER

(71) Applicant: HORIBA, Ltd., Kyoto (JP)

(72) Inventors: Kengo Yasui, Kyoto (JP); Kazutaka Okamoto, Kyoto (JP); Shuji Takada, Kyoto (JP)

(73) Assignee: HORIBA, Ltd. (JP)

( * ) Notice: Subject to any disclaimer, the term of this patent is extended or adjusted under 35 U.S.C. 154(b) by 0 days.

(21) Appl. No.: 14/071,155

(22) Filed: Nov. 4, 2013

(65) Prior Publication Data

US 2014/0124665 A1    May 8, 2014

(30) Foreign Application Priority Data

Nov. 2, 2012  (JP) ................. 2012-242927

(51) Int. Cl.
*G01T 1/24* (2006.01)
*H01J 37/285* (2006.01)
*H01J 37/244* (2006.01)
*G01N 23/223* (2006.01)

(52) U.S. Cl.
CPC .............. *G01T 1/241* (2013.01); *H01J 37/285* (2013.01); *G01T 1/244* (2013.01); *H01J 37/244* (2013.01); *G01N 23/223* (2013.01)
USPC ....................... 250/397; 250/336.1

(58) Field of Classification Search
USPC .......... 250/397, 336.1, 338.4, 339.03, 370.01
See application file for complete search history.

(56) References Cited

U.S. PATENT DOCUMENTS

| 8,334,511 | B2 * | 12/2012 | Schamber et al. ............ 250/311 |
| 8,558,175 | B2 * | 10/2013 | Kromer ....................... 250/336.1 |
| 2010/0163742 | A1 | 7/2010 | Watanabe et al. |
| 2012/0132818 | A1 * | 5/2012 | Falke et al. .............. 250/370.01 |

FOREIGN PATENT DOCUMENTS

| JP | 10-282373 A | 10/1998 |
| JP | 2000-138393 A | 5/2000 |
| JP | 2001-284606 A | 10/2001 |
| JP | 2010-169659 A | 8/2010 |

* cited by examiner

*Primary Examiner* — Kiet T Nguyen
(74) *Attorney, Agent, or Firm* — Cantor Colburn LLP

(57) ABSTRACT

A radiation detector employed in a radiation detection apparatus and a fluorescent X-ray analyzer includes: a first circuit board on which a semiconductor radiation sensor is mounted and which is cooled by a Peltier device (an electronic cooling unit); and a second circuit board set apart from the first circuit board. A plurality of lead pins are joined to the second circuit board. Then, the first circuit board and the second circuit board are wire-bonded to each other. In comparison with conventional wire bonding performed onto the tips of lead pins, the work of connection is easy, the productivity is high, and the reliability of connection is high. Further, the second circuit board not requiring cooling is set apart so that cooling is concentrated on the first circuit board. This permits size reduction of the radiation detector.

7 Claims, 10 Drawing Sheets

F I G. 3
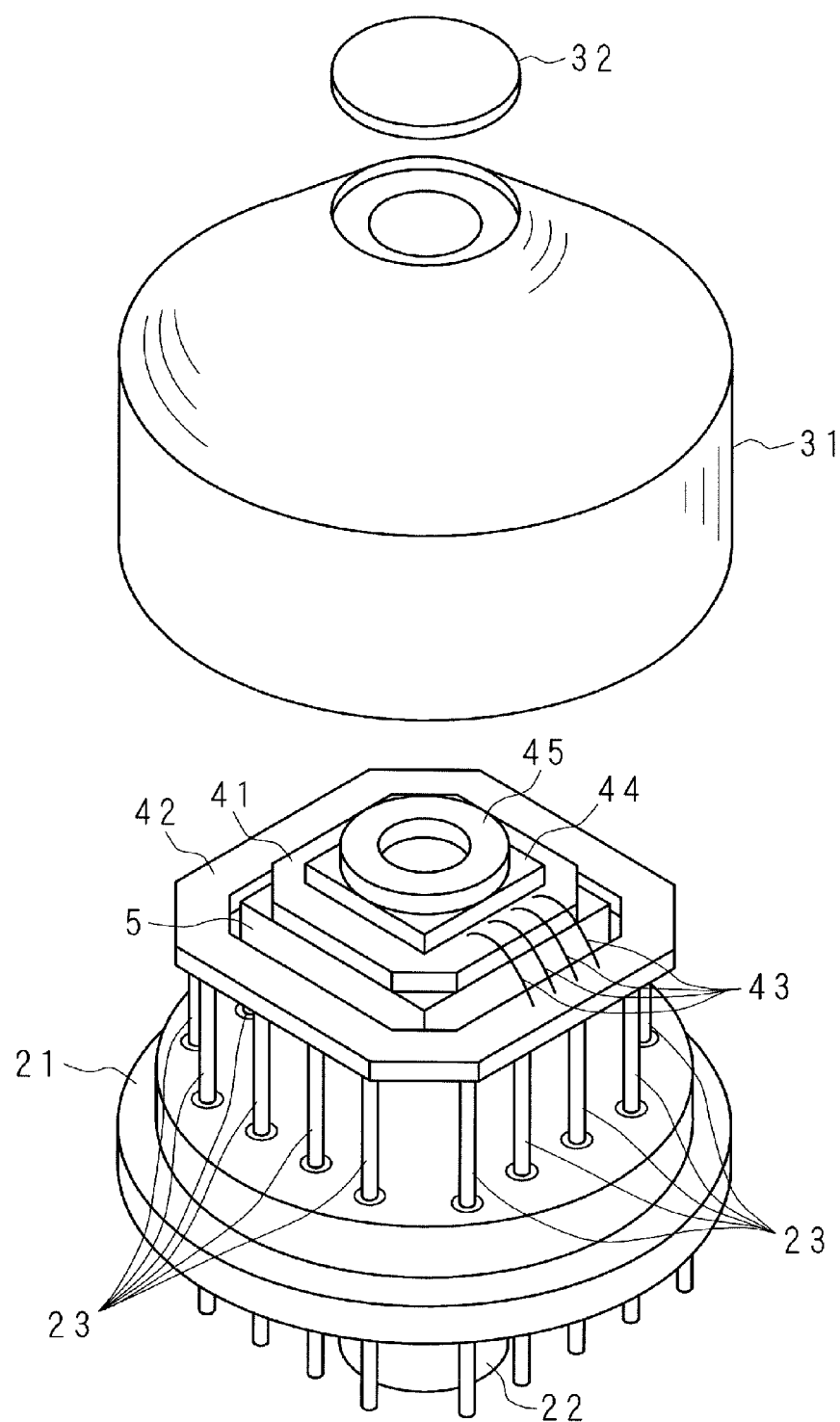

RADIATION DETECTOR, RADIATION DETECTION APPARATUS, AND X-RAY ANALYZER

CROSS-REFERENCE TO RELATED APPLICATIONS

This Nonprovisional application claims priority under 35 U.S.C. §119(a) on Patent Application No. 2012-242927 filed in Japan on Nov. 2, 2012, the entire contents of which are hereby incorporated by reference.

BACKGROUND

1. Technical Field

The present invention relates to a radiation detector, a radiation detection apparatus, and an X-ray analyzer, which employ a semiconductor radiation sensor.

2. Description of Related Art

In some radiation detectors detecting radiation such as X-ray, a semiconductor radiation sensor such as an SDD (Silicon Drift Detector) is employed so as to detect radiation. In some cases, such a semiconductor radiation sensor is used in a cooled state for the purpose of increasing the detection sensitivity. For example, a Peltier device is employed for cooling. In a radiation detector employing a Peltier device is, the hot side of the Peltier device is joined to a metal stem serving as a base. Then, a circuit board on which the semiconductor radiation sensor is mounted is joined to the cold side of the Peltier device. Further, the entirety is sealed by a metal cover and constructed in the form of a package. The inside of the package is depressurized or alternatively filled with inert gas. The radiation detector has a plurality of lead pins used for inputting and outputting signals. Then, the tips of the individual lead pins are connected to the circuit board by wire bonding. A radiation detector having such a configuration is described in Japanese Patent Application Laid-Open No. 2000-138393.

SUMMARY OF THE INVENTION

In a conventional radiation detector, the work of connecting the tips of a plurality of lead pins to a circuit board by wire bonding has been difficult and hence the productivity has been low. Further, a problem of low reliability of connection has arisen.

The present invention has been devised in view of such a situation. An object thereof is to provide a radiation detector, a radiation detection apparatus, and an X-ray analyzer in which the connection method for the circuit board and the lead pins is improved so that the productivity and the reliability are improved and hence a large number of components are allowed to be mounted and size reduction is achievable.

A radiation detector according to the present invention is characterized by comprising: a semiconductor radiation sensor; an electronic cooling unit cooling the semiconductor radiation sensor; a plurality of lead pins; a first circuit board on which the semiconductor radiation sensor is mounted and which is in thermal contact with a cold side of the electronic cooling unit; and a second circuit board which is not in thermal contact with the electronic cooling unit and is set apart from the first circuit board, wherein the plurality of lead pins are joined to the second circuit board, and the first circuit board and the second circuit board are electrically connected to each other.

The radiation detector according to the present invention is characterized in that the second circuit board is set apart from a plane containing a surface of the first circuit board and is arranged opposite to the semiconductor radiation sensor with respect to the plane.

The radiation detector according to the present invention is characterized in that tips of the plurality of lead pins are joined to one surface of the second circuit board.

The radiation detector according to the present invention is characterized in that a capacitor is mounted on the second circuit board.

A radiation detection apparatus according to the present invention is characterized by comprising: a radiation detector according to the present invention, outputting a signal corresponding to energy of detected radiation; and a spectrum generating unit for generating a spectrum of the radiation on the basis of the signal outputted by the radiation detector.

An X-ray analyzer according to the present invention is characterized by comprising: an X-ray source for projecting X-ray onto a sample; and a radiation detection apparatus according to the present invention, detecting X-ray fluorescence generated by the sample.

An X-ray analyzer according to the present invention is characterized by comprising: a radiation source for projecting an electron beam onto a sample; and a radiation detection apparatus according to the present invention, detecting characteristic X-ray generated by the sample.

In the present invention, the radiation detector employed in the radiation detection apparatus and the fluorescent X-ray analyzer includes: a first circuit board on which a semiconductor radiation sensor is mounted and which is cooled by an electronic cooling unit; and a second circuit board set apart from the first circuit board. A plurality of lead pins are joined to the second circuit board. Then, the first circuit board and the second circuit board are wire-bonded to each other. By virtue of the joining of the lead pins to the second circuit board and the wire bonding between the first circuit board and the second circuit board, the semiconductor radiation sensor is connected to the outside of the radiation detector.

Further, in the present invention, in the radiation detector, the second circuit board is set apart from a plane containing the surface of the first circuit board and is arranged opposite to the semiconductor radiation sensor with respect to the plane. In this configuration, the semiconductor radiation sensor is located closer to the measuring object than the other parts.

Further, in the present invention, the tips of the plurality of lead pins are joined electrically and physically to one surface of the second circuit board. Thus, the work of joining is easy and the plurality of lead pins are fixed to the second circuit board.

Further, in the present invention, a capacitor is mounted on the second circuit board set apart from the first circuit board. Thus, the capacitor that could cause a system peak is set apart from the semiconductor radiation sensor.

In the present invention, a radiation detector is realized in which the work of connection is easier than in the conventional art so that the productivity and the reliability are high. Further, the present invention has excellent effects, for example, that size reduction of the radiation detector is achievable and that the radiation detector is allowed to be set close to a target of radiation measurement so that the efficiency of radiation detection is improved.

The above and further objects and features of the invention will more fully be apparent from the following detailed description with accompanying drawings.

BRIEF DESCRIPTION OF THE SEVERAL VIEWS OF THE DRAWINGS

FIG. 3 is a schematic exploded perspective view of a radiation detector according to Embodiment 1;

DETAILED DESCRIPTION

The present invention is described below in detail with reference to the drawings illustrating embodiments.

(Embodiment 1)

Figure 1:
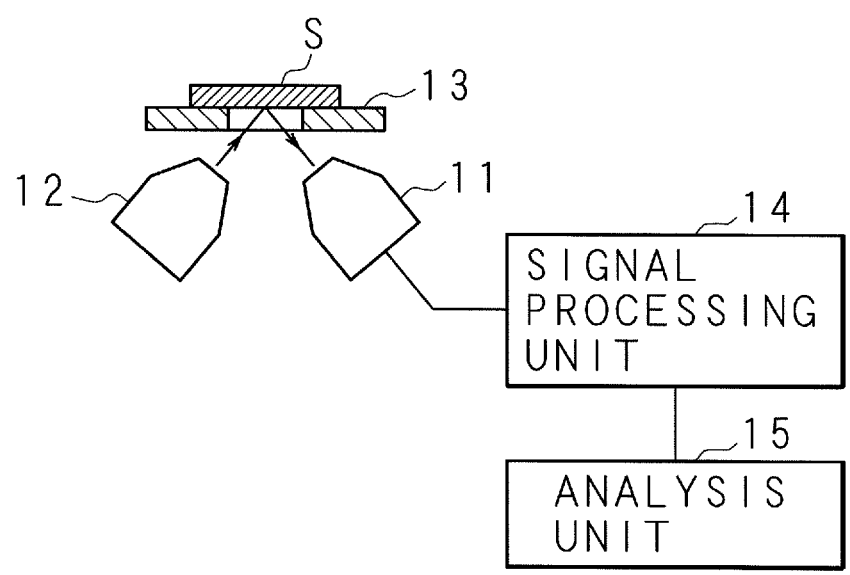
FIG. 1 is a block diagram illustrating a configuration of a fluorescent X-ray analyzer.

FIG. 1 is a block diagram illustrating the configuration of a fluorescent X-ray analyzer. The fluorescent X-ray analyzer includes: an X-ray source 12 irradiating a sample S with X-ray; a sample stage 13 onto which the sample S is placed; and a radiation detector 11 according to the present embodiment. FIG. 1 illustrates a cross section of the sample stage 13 and the sample S. The X-ray source 12, the sample stage 13, and the radiation detector 11 are arranged in a housing (not illustrated) for cutting off the X-ray. For example, the X-ray source 12 is composed of an X-ray tube. X-ray are projected from the X-ray source 12 onto the sample S, then X-ray fluorescence are generated by the sample S, and then the radiation detector 11 detects the X-ray fluorescence generated by the sample S. In FIG. 1, the X-ray projected from the X-ray source 12 onto the sample S and the X-ray fluorescence generated by the sample S and then detected by the radiation detector 11 are indicated by arrows. The radiation detector 11 outputs a signal proportional to the energy of the detected fluorescent X-ray. The radiation detector 11 is connected to a signal processing unit 14 processing the outputted signal. The signal processing unit 14 counts the signal of each value outputted by the radiation detector 11 so as to perform the processing of acquiring the relation between the energy of the fluorescent X-ray and the number of counts, that is, the spectrum of the X-ray fluorescence. The combination of the radiation detector 11 and the signal processing unit 14 corresponds to the radiation detection apparatus of the present invention. The fluorescent X-ray analyzer corresponds to the X-ray analyzer of the present invention. Then, the radiation detection apparatus detects the X-ray fluorescence as characteristic X-ray. The signal processing unit 14 is connected to an analysis unit 15. The analysis unit 15 is constructed from a computer such as a personal computer and performs qualitative analysis or quantitative analysis on the composition of the sample S on the basis of the spectrum of the X-ray fluorescence generated by the signal processing unit 14.

Figure 2:
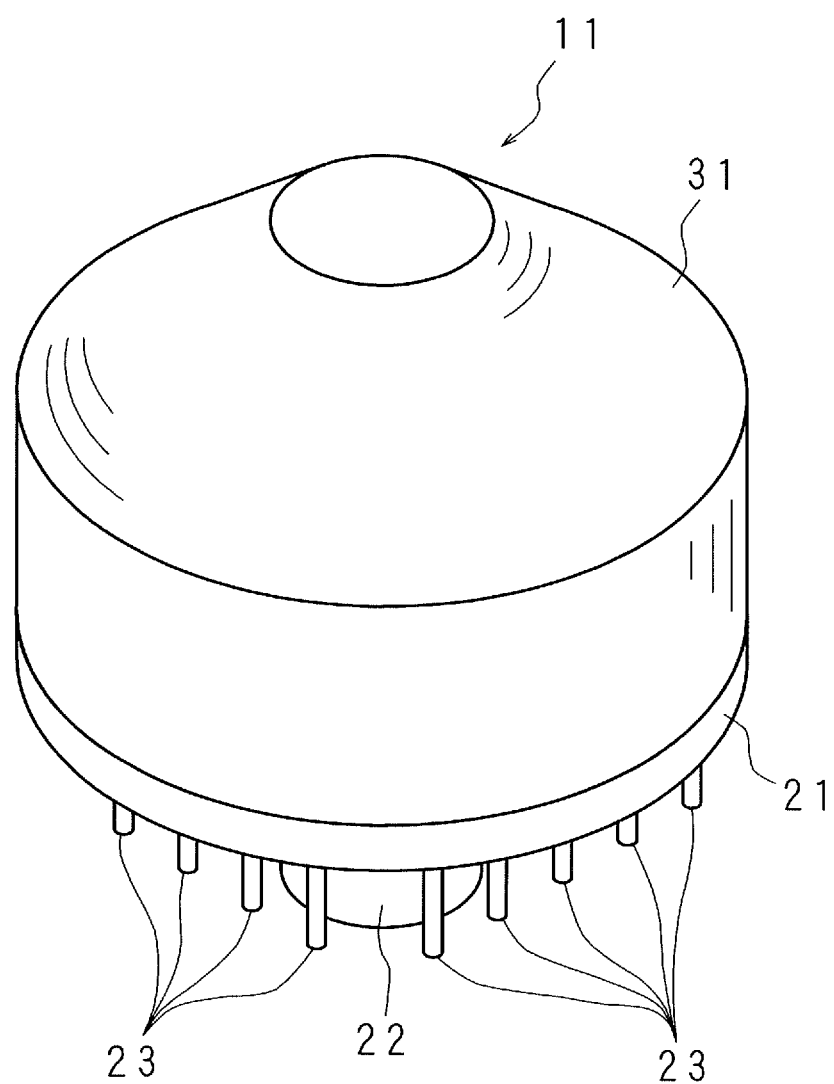
FIG. 2 is a schematic perspective view of a radiation detector according to Embodiment 1.

FIG. 2 is a schematic perspective view of the radiation detector 11 according to Embodiment 1. FIG. 3 is a schematic exploded perspective view of the radiation detector 11 according to Embodiment 1. The majority of the components of the radiation detector 11 are provided on the surface side of a stem base 21 having a disk shape. The stem base 21 is a member serving as a base of the radiation detector 11 and is formed from metal. On the surface of the stem base 21, a Peltier device (an electronic cooling unit) 5 is arranged and the Peltier device 5 is in contact with a first circuit board 41. Then, a semiconductor radiation sensor 44 is mounted on the surface of the first circuit board 41 and then a collimator 45 is arranged on the surface of the semiconductor radiation sensor 44. For example, the semiconductor radiation sensor 44 is composed of an SDD. Further, a second circuit board 42 is arranged at a position not in contact with the Peltier device 5. A bolt 22 protrudes on the back side of the stem base 21. In the bolt 22, a groove (not illustrated) is formed and used for fixing the radiation detector 11. For example, the bolt 22 is linked to a heat radiation plate in the outside of the radiation detector 11. Further, a plurality of lead pins 23 penetrating the stem base 21 are provided for the purpose of supply of electricity and input and output of the signals.

On the surface side of the stem base 21, a cover 31 is placed. The surface of the stem base 21, the portion of the lead pins 23 protruding toward the surface side of the stem base 21, the Peltier device 5, the first circuit board 41, the second circuit board 42, the semiconductor radiation sensor 44, and the collimator 45 are covered by the cover 31. The cover 31 has a shape obtained by linking a truncated cone to one end of a cylinder. Then, the other end of the cylinder is sealed in contact with the stem base 21. In the truncated portion at the tip of the cover 31, a window 32 is provided that is formed from an X-ray transmitting material such as beryllium. The window 32 faces the radiation detector 11 and the collimator 45. The inner side of the cover 31 is sealed and then depressurized or alternatively filled with inert gas.

Figure 4:
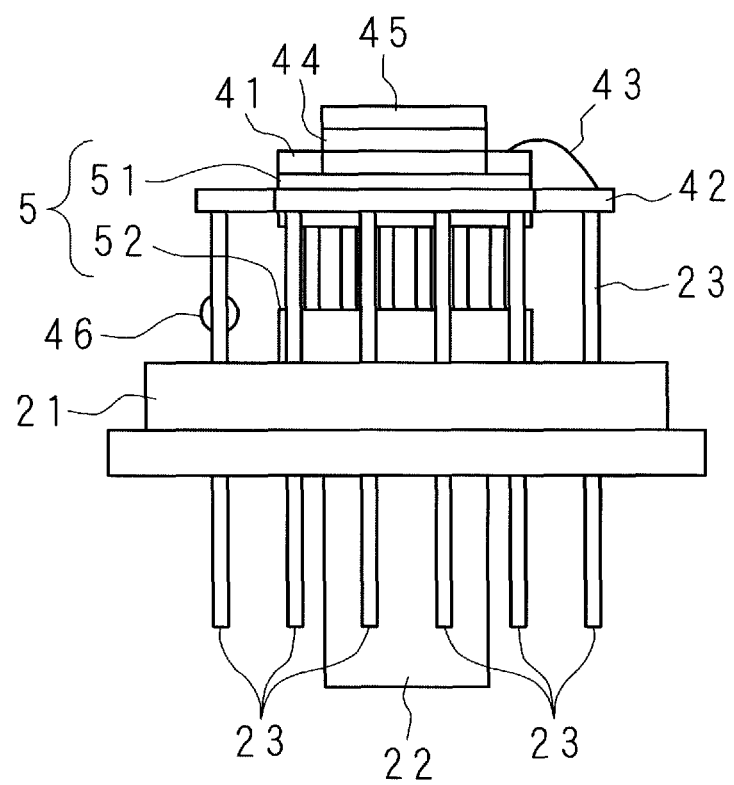
FIG. 4 is a schematic front view of a radiation detector according to Embodiment 1, where a cover is removed.
Figure 5:
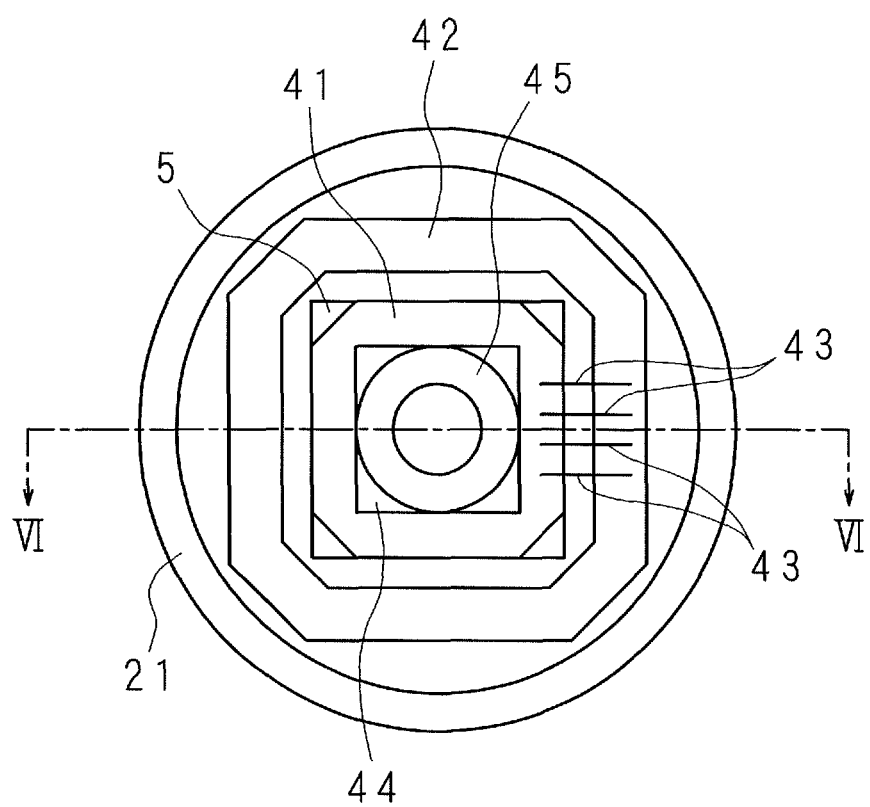
FIG. 5 is a schematic plan view of a radiation detector according to Embodiment 1, where a cover is removed.
Figure 6:
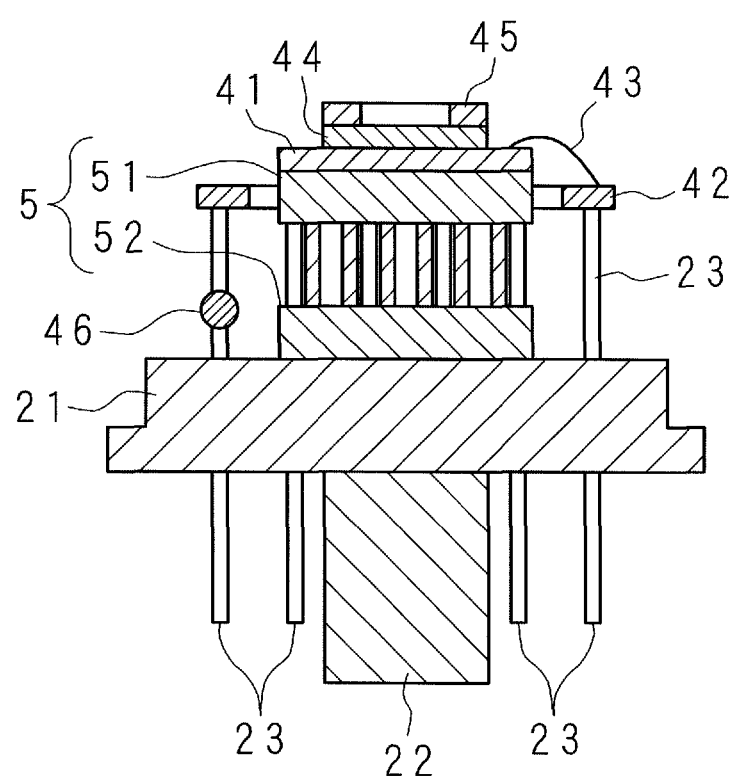
FIG. 6 is a schematic sectional view taken along line VI-VI in FIG. 5.

FIG. 4 is a schematic front view of the radiation detector 11 according to Embodiment 1, where the cover 31 is removed. FIG. 5 is a schematic plan view of the radiation detector 11 according to Embodiment 1, where the cover 31 is removed. FIG. 6 is a schematic sectional view taken along line VI-VI in FIG. 5. The hot side 52 of the Peltier device 5 is in thermal contact with the surface of the stem base 21. For example, the hot side 52 is joined to the surface of the stem base 21 by using heat conductive adhesives such as solder. Another heat conductive member may be provided between the surface of the stem base 21 and the hot side 52. The rear face of the first circuit board 41 is in thermal contact with the cold side 51 of the Peltier device 5. For example, the rear face of the first circuit board 41 is adhered to the cold side 51 by using heat conductive adhesives. Another heat conductive member may be provided between the rear face of the first circuit board 41 and the cold side 51. The first circuit board 41 is almost in parallel to the surface of the stem base 21.

The semiconductor radiation sensor 44 is mounted on the surface of the first circuit board 41. Among the components other than the semiconductor radiation sensor 44, components requiring cooling are provided on the first circuit board 41. For example, a preamplifier is provided on the first circuit board 41. The semiconductor radiation sensor 44 is cooled through the first circuit board 41 by the Peltier device 5. The heat is transferred from the hot side 52 of the Peltier device 5 to the stem base 21, then transferred from the stem base 21 to the bolt 22, and then radiated from the bolt 22 to the outside. The collimator 45 arranged on the surface of the semiconductor radiation sensor 44 is provided with a through hole. The X-ray fluorescence having passed through the window 32 enter the semiconductor radiation sensor 44 through the through hole of the collimator 45.

In the surroundings of the Peltier device 5, the plurality of lead pins 23 penetrating the stem base 21 stand apart from the Peltier device 5. The plurality of lead pins 23 are almost in parallel to each other and insulated electrically and thermally from the stem base 21. Further, a second circuit board 42 having an annular shape in plan view is arranged such as to surround the Peltier device 5. The second circuit board 42 is set apart from the Peltier device 5 and the first circuit board 41 in a direction parallel to the surface and is arranged at a position not overlapping in a direction perpendicular to the surface of the first circuit board 41. Since being set apart from the Peltier device 5, the second circuit board 42 is not cooled by the Peltier device 5. The second circuit board 42 is provided with components not requiring cooling. For example, a capacitor serving as a countermeasure against static electricity is provided on the second circuit board 42. Further, as illustrated in FIGS. 4 and 6, the second circuit board 42 is arranged at a position closer to the surface of the stem base 21 than the first circuit board 41. Thus, the first circuit board 41 protrudes from the surface of the stem base 21 relative to the second circuit board 42. Accordingly, the positional relation of the first circuit board 41 and the second circuit board 42 is such that the second circuit board 42 is set apart from a plane containing the surface of the first circuit board 41 and then the second circuit board 42 and the semiconductor radiation sensor 44 are arranged opposite to each other with respect to the plane containing the surface of the first circuit board 41.

The plurality of lead pins 23 are joined to the second circuit board 42. More specifically, the tips of the plurality of lead pins 23 are joined to the rear face of the second circuit board 42 by a method such as soldering in such a manner that the wiring formed on the second circuit board 42 is brought into electric conduction to the lead pins 23. As such, the plurality of lead pins 23 are physically linked to the second circuit board 42 and, at the same time, the plurality of lead pins 23 and the second circuit board 42 are electrically connected to each other. Here, the plurality of lead pins 23 may be joined to the second circuit board 42 in such a manner that the tips penetrate the second circuit board 42.

Further, the first circuit board 41 and the second circuit board 42 are connected to each other by wire bonding or the like through a plurality of wires 43. Thus, the semiconductor radiation sensor 44 is connected to the plurality of lead pins 23 via the first circuit board 41, the plurality of wires 43, and the second circuit board 42. The plurality of lead pins 23 are connected to an electric power source (not illustrated), the signal processing unit 14, and the like in the outside of the radiation detector 11. A voltage necessary for operation is applied on the semiconductor radiation sensor 44 from the outside of the radiation detector 11 via the plurality of lead pins 23. Further, the semiconductor radiation sensor 44 outputs a signal corresponding to the energy of incident fluorescent X-ray. The signal outputted by the semiconductor radiation sensor 44 is amplified by the preamplifier mounted on the first circuit board 41 and then outputted through the plurality of lead pins 23 to the signal processing unit 14.

Further, a getter 46 is provided on the surface of the stem base 21. The getter 46 is connected to two of the lead pins 23. When a current is supplied through the lead pins 23, the getter 46 adsorbs impurity gas such as moisture contained in the gas sealed by the cover 31. Since the getter 46 adsorbs impurities in the gas, the semiconductor radiation sensor 44 is cooled efficiently by the Peltier device 5.

As described above in detail, in the present embodiment, the radiation detector 11 includes: the first circuit board 41 on which the semiconductor radiation sensor 44 is mounted and which is cooled by the Peltier device 5; and the second circuit board 42 set apart from the first circuit board 41. The plurality of lead pins 23 are joined to the second circuit board 42. Then, the first circuit board 41 and the second circuit board 42 are wire-bonded to each other. In the connection by means of joining between the plurality of lead pins 23 and the second circuit board 42 and the wire bonding between the first circuit board 41 and the second circuit board 42, the work of connection is easy and achieves a high productivity in comparison with conventional wire bonding performed onto the tips of lead pins. Further, wire bonding is performed on the second circuit board 42 to which the plurality of lead pins 23 have been joined. Thus, in comparison with the conventional art that wire bonding is performed on each lead pin, loss of ultrasonic waves in the work of wire bonding is avoided and hence reliable connection is achieved. Further, since the second circuit board 42 on which components not requiring cooling are mounted is provided separately from the first circuit board 41, the first circuit board 41 provided with cooling-requiring components including the semiconductor radiation sensor 44 is cooled intensively by the Peltier device 5. This permits size reduction of the Peltier device 5. A large number of components not requiring cooling are allowed to be mounted on the second circuit board 42 and, on the other hand, the first circuit board 41 is allowed to be fabricated smaller than the conventional circuit board and size reduction of the Peltier device 5 also is allowed. This permits size reduction of the radiation detector 11 in comparison with the conventional art. When size reduction of the radiation detector 11 is achieved, the radiation detector 11 is allowed to be set closer to the sample S in comparison with the conventional art. This improves the efficiency of radiation detection in the radiation detection apparatus and hence improves the precision of analysis in the fluorescent X-ray analyzer.

Further, in the present embodiment, the first circuit board 41 is arranged in a manner of protruding from the surface of the stem base 21 relative to the second circuit board 42. This protruding of the first circuit board 41 is allowed because the first circuit board 41 and the second circuit board 42 are separated from each other. When the first circuit board 41 provided with a minimal number of components including the semiconductor radiation sensor 44 is set protruding, a configuration is allowed that the semiconductor radiation sensor 44 protrudes relative to almost all of the other parts so that the semiconductor radiation sensor 44 is set closer to the sample S. When the semiconductor radiation sensor 44 is set close to the sample S, this improves the efficiency of radiation detection in the radiation detection apparatus and hence improves the precision of analysis in the fluorescent X-ray analyzer. Further, in the present embodiment, the second circuit board 42 on which components not requiring cooling such as a capacitor are mounted is set apart from the first circuit board 41. This reduces a possibility that X-ray fluorescence generated by the second circuit board 42 itself or by the components mounted on the second circuit board 42 enter the semiconductor radiation sensor 44 so as to generate a system peak. This permits precision detection of X-ray fluorescence.

(Embodiment 2)

Figure 7:
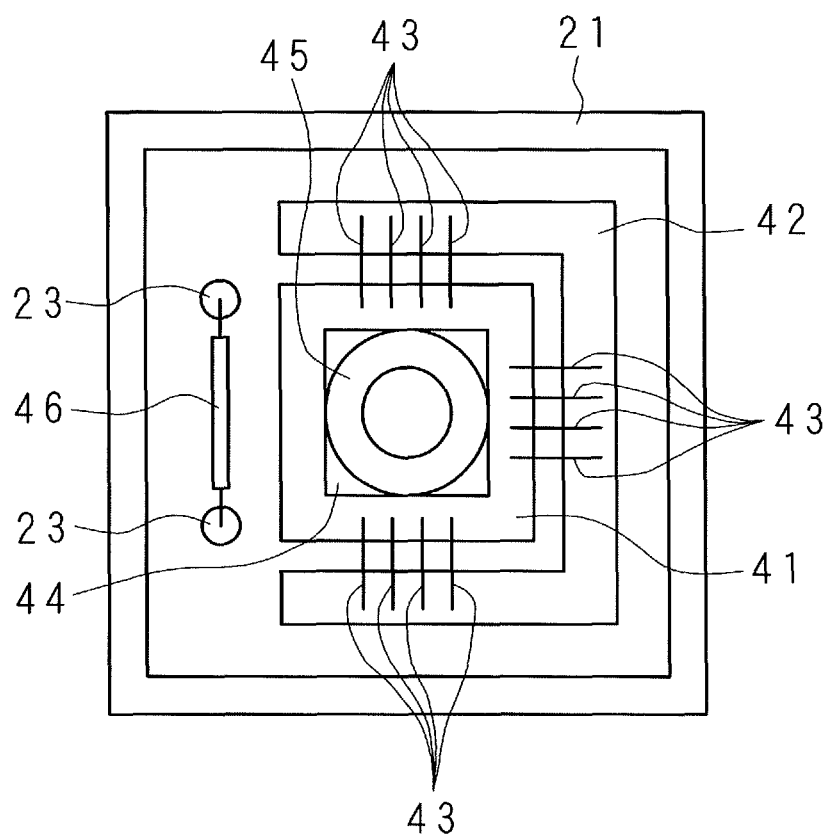
FIG. 7 is a schematic plan view of a radiation detector according to Embodiment 2, where a cover is removed.
Figure 8:
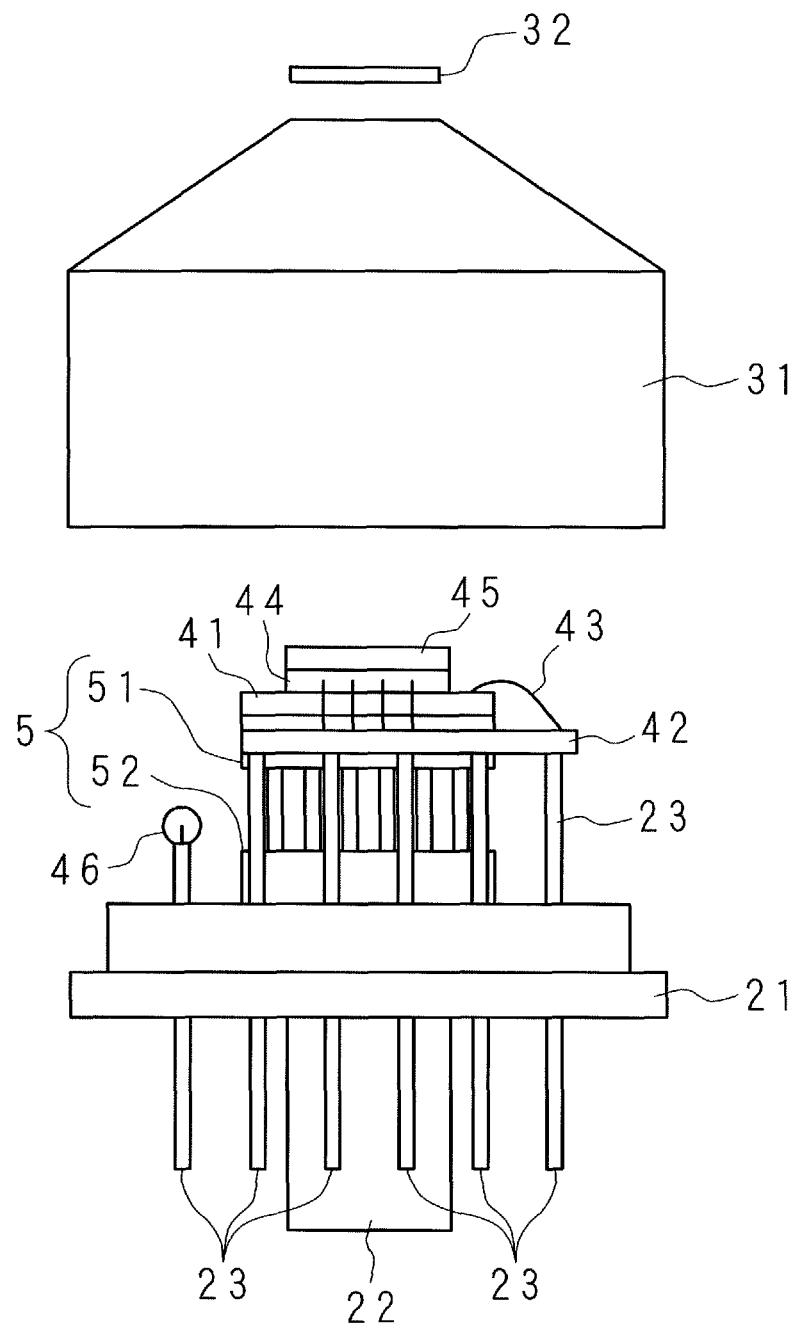
FIG. 8 is a schematic exploded front view of a radiation detector according to Embodiment 2.

FIG. 7 is a schematic plan view of a radiation detector 11 according to Embodiment 2, where a cover 31 is removed. FIG. 8 is a schematic exploded front view of the radiation detector 11 according to Embodiment 2. The stem base 21 has a rectangular plate shape. The hot side 52 of the Peltier device 5 is in thermal contact with the surface of the stem base 21. Then, the first circuit board 41 on which the semiconductor radiation sensor 44 is mounted is in thermal contact with the cold side 51 of the Peltier device 5. The second circuit board 42 is formed in a U-shape in plan view and arranged at a position of enclosing three sides of the first circuit board 41 in plan view. In the surroundings of the Peltier device 5, the plurality of lead pins 23 penetrating the stem base 21 are standing and the plurality of lead pins 23 are joined to the second circuit board 42. The first circuit board 41 and the second circuit board 42 are wire-bonded to each other through the plurality of wires 43. The getter 46 is arranged in a portion not enclosed by the second circuit board 42 in plan view in the surrounding of the first circuit board 41. The getter 46 is connected to two of the lead pins 23. The surface of the stem base 21, the portion of the lead pins 23 protruding toward the surface side of the stem base 21, the Peltier device 5, the first circuit board 41, the second circuit board 42, the semiconductor radiation sensor 44, the collimator 45, and the getter 46 are covered by the cover 31. The cover 31 has a shape obtained by linking a quadrilateral frustum to one end of a quadrilateral tube. Then, the other end of the quadrilateral tube is sealed in contact with the stem base 21. The window 32 is provided at the tip of the cover 31.

Also in the present embodiment, the plurality of lead pins 23 are joined to the second circuit board 42. Then, the first circuit board 41 and the second circuit board 42 are wire-bonded to each other. Thus, similarly to Embodiment 1, in comparison with the conventional art, the work of wire bonding is easy, the productivity is high, and the reliability of connection is high. Further, similarly, size reduction of the radiation detector 11 is achieved in comparison with the conventional art.

(Embodiment 3)

Figure 9:
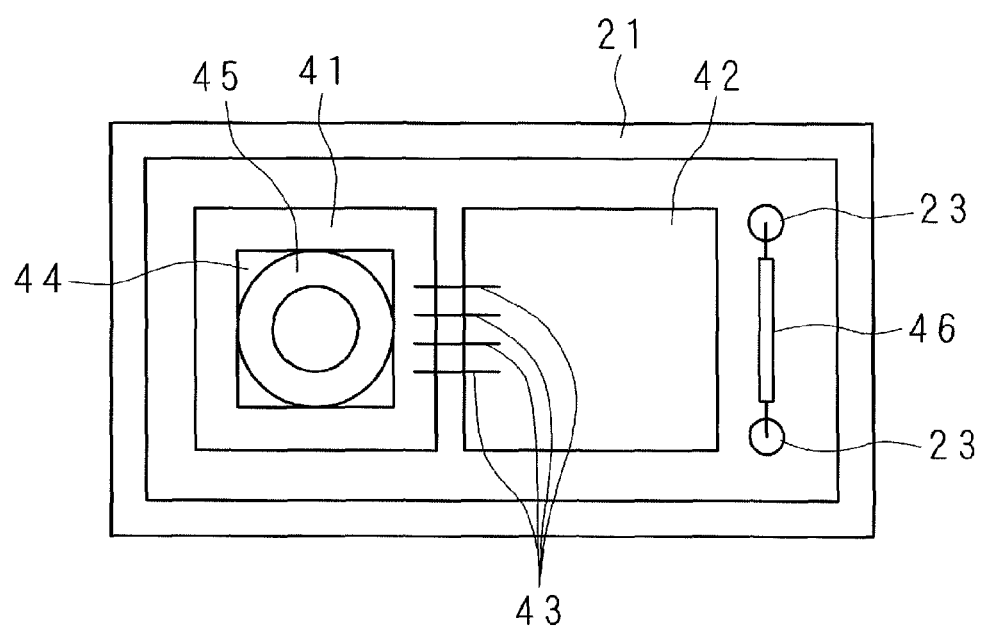
FIG. 9 is a schematic plan view of a radiation detector according to Embodiment 3, where a cover is removed.
Figure 10:
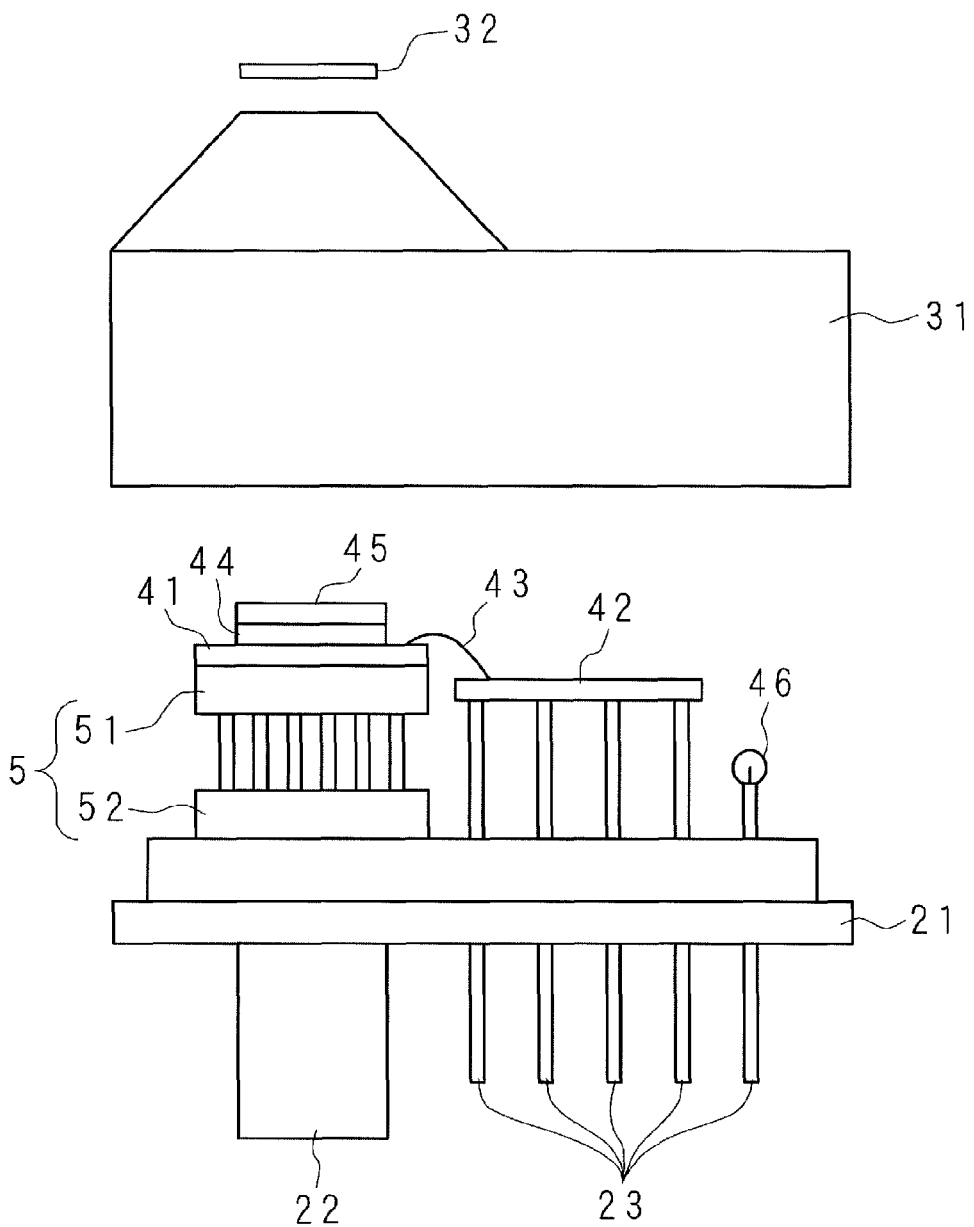
FIG. 10 is a schematic exploded front view of a radiation detector according to Embodiment 3.

FIG. 9 is a schematic plan view of a radiation detector 11 according to Embodiment 3, where a cover 31 is removed. FIG. 10 is a schematic exploded front view of the radiation detector 11 according to Embodiment 3. The stem base 21 has a rectangular plate shape in plan view. The second circuit board 42 is formed in a rectangular shape in plan view. Then, the first circuit board 41 and the second circuit board 42 are arranged in line in the longitudinal direction of the stem base 21 in plan view. The hot side 52 of the Peltier device 5 is in thermal contact with a part of the surface of the stem base 21. Then, the first circuit board 41 on which the semiconductor radiation sensor 44 is mounted is in thermal contact with the cold side 51 of the Peltier device 5. The plurality of lead pins 23 penetrating the stem base 21 stand in plural lines in the longitudinal direction of the stem base 21. Then, the plurality of lead pins 23 are joined to the second circuit board 42. The first circuit board 41 and the second circuit board 42 are wire-bonded to each other through the plurality of wires 43. The first circuit board 41 protrudes from the surface of the stem base 21 relative to the second circuit board 42. In the surface of the stem base 21, the getter 46 is arranged in a portion located adjacent to the second circuit board 42 in plan view. The getter 46 is connected to two of the lead pins 23. The surface of the stem base 21, the portion of the lead pins 23 protruding toward the surface side of the stem base 21, the Peltier device 5, the first circuit board 41, the second circuit board 42, the semiconductor radiation sensor 44, the collimator 45, and the getter 46 are covered by the cover 31. Then, the end of the cover 31 is sealed in contact with the stem base 21. The portion of the cover 31 facing the first circuit board 41 has a truncated tapered shape and the window 32 is provided at the tip.

Also in the present embodiment, the plurality of lead pins 23 are joined to the second circuit board 42. Then, the first circuit board 41 and the second circuit board 42 are wire-bonded to each other. Thus, similarly to Embodiment 1, in comparison with the conventional art, the work of wire bonding is easy, the productivity is high, and the reliability of connection is high. Further, similarly, a configuration is allowed that the semiconductor radiation sensor 44 is set closer to the sample S.

Here, the above-mentioned Embodiments 1 to 3 have been described for an example that the electronic cooling unit is composed of the single Peltier device 5. Instead, the radiation detector 11 may be of a mode that the electronic cooling unit is constructed from a plurality of Peltier devices. Further, Embodiments 1 to 3 have been described for a mode that the radiation detection apparatus is built in the fluorescent X-ray analyzer. Instead, a mode may be employed that the radiation detection apparatus is separated from the other parts of the fluorescent X-ray analyzer. Further, Embodiments 1 to 3 have been described for a mode that the X-ray analyzer is composed of the fluorescent X-ray analyzer. Instead, the X-ray analyzer may be of another mode that radiation such as an electron beam other than X-ray is projected onto a sample and then characteristic X-ray generated by the sample are detected by the radiation detection apparatus. Further, Embodiments 1 to 3 have been described for a mode that the radiation detection apparatus detects X-ray. Instead, a mode may be employed that the radiation detection apparatus detects radiation other than X-ray.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A radiation detector comprising:
   a semiconductor radiation sensor;
   an electronic cooling unit cooling the semiconductor radiation sensor;
   a plurality of lead pins;
   a first circuit board on which the semiconductor radiation sensor is mounted and which is in thermal contact with a cold side of the electronic cooling unit; and
   a second circuit board which is not in thermal contact with the electronic cooling unit and is set apart from the first circuit board,
   wherein the plurality of lead pins are joined to the second circuit board, and
   the first circuit board and the second circuit board are electrically connected to each other.

2. The radiation detector according to claim 1,
   wherein the second circuit board is set apart from a plane containing a surface of the first circuit board and is arranged opposite to the semiconductor radiation sensor with respect to the plane.

3. The radiation detector according to claim 1,
   wherein tips of the plurality of lead pins are joined to one surface of the second circuit board.

4. The radiation detector according to claim 1,
   wherein a capacitor is mounted on the second circuit board.

5. A radiation detection apparatus comprising:
   a radiation detector according to claim 1, outputting a signal corresponding to energy of detected radiation; and
   a spectrum generating unit for generating a spectrum of the radiation on the basis of the signal outputted by the radiation detector.

6. An X-ray analyzer comprising:
   an X-ray source for projecting X-ray onto a sample; and
   a radiation detection apparatus according to claim 5, detecting X-ray fluorescence generated by the sample.

7. An X-ray analyzer comprising:
a radiation source for projecting an electron beam onto a sample; and
a radiation detection apparatus according to claim 5, detecting characteristic X-ray generated by the sample.

* * * * *